United States Patent [19]

Fuchs et al.

[11] 4,350,630
[45] Sep. 21, 1982

[54] CONTINUOUS EXTRACTION OF CAPROLACTAM FROM AN AQUEOUS SOLUTION CONTAINING CAPROLACTAM AND ITS OLIGOMERS

[75] Inventors: Hugo Fuchs, Ludwigshafen; Uwe Brand, Rosengarten; Ernst Deuker, Gruenstadt; Elmar Frommer, Ludwigshafen, all of Fed. Rep. of Germany

[73] Assignee: BASF Aktiengesellschaft, Fed. Rep. of Germany

[21] Appl. No.: 276,815

[22] Filed: Jun. 25, 1981

[30] Foreign Application Priority Data

Jul. 12, 1980 [DE] Fed. Rep. of Germany ....... 3026538

[51] Int. Cl.$^3$ ............................................ C07D 201/16
[52] U.S. Cl. ............................................... 260/239.3 A
[58] Field of Search .................................. 260/239.3 A

[56] References Cited

U.S. PATENT DOCUMENTS 2,758,991 8/1956 Kretzers et al. ............. 260/239.3 A
3,264,060 8/1966 Nieswandt et al. .................... 23/119
3,359,290 12/1967 Roberts et al. .............. 260/239.3 A
4,036,830 7/1977 De Rooij et al. ............ 260/239.3 A
4,051,113 9/1977 Kissel .................................... 260/78
4,154,729 5/1979 Fuchs et al. ................. 260/239.3 X

FOREIGN PATENT DOCUMENTS 9215 2/1955 German Democratic Rep. .
2656182 6/1978 Fed. Rep. of Germany .
1251258 10/1971 United Kingdom .

*Primary Examiner*—Robert T. Bond
*Attorney, Agent, or Firm*—Keil & Witherspoon

[57] ABSTRACT

In a process for continuously extracting caprolactam from an aqueous solution, containing caprolactam and its oligomers, with organic solvents, by introducing the aqueous solution into the upper part of an extraction zone and organic solvents into the lower part, and taking off a solution of caprolactam in organic solvents at the upper end and an aqueous phase containing caprolactam oligomers at the lower end, the improvement that liquid aromatic hydrocarbons are used and the extraction is carried out at a pH of from 2.0 to 6.0.

4 Claims, No Drawings

CONTINUOUS EXTRACTION OF CAPROLACTAM FROM AN AQUEOUS SOLUTION CONTAINING CAPROLACTAM AND ITS OLIGOMERS

The extraction of polycaprolactam with water to remove monomer gives aqueous solutions containing caprolactam and its oligomers. It is necessary to recover monomeric caprolactam from the solutions in which it is present.

East German Patent 9,215 discloses a method wherein caprolactam-containing wash waters are first partially concentrated, oligomers which hereupon precipitate are filtered off, the filtrate is extracted with solvents and the caprolactam is isolated from the solvent phase. However, this method has a high energy consumption, and furthermore filtering off the precipitated oligomers presents difficulties. According to German Laid-Open Application DOS No. 1,770,088, the extraction of caprolactam-containing wash waters is carried out with a water-immiscible solvent, the partition coefficient of caprolactam in the solvent/water system at 25° C. being not less than 0.2, and the solvent having a lower density than the aqueous phase or a higher density than the oligomeric solids. However, in realizing this process in continuous operation, the oligomeric solids always cause difficulties, and in particular the extraction columns become blocked.

It is an object of the present invention to provide a method of extracting caprolactam from aqueous solutions containing caprolactam and its oligomers, which proceeds smoothly and in which the oligomers do not present problems.

We have found that this object is achieved by a process for continuously extracting caprolactam from an aqueous solution, containing caprolactam and its oligomers, with organic solvents, by introducing the aqueous solution into the upper part of an extraction zone and organic solvents into the lower part, and taking off a solution of caprolactam in organic solvents at the upper end and an aqueous phase containing caprolactam oligomers at the lower end, wherein liquid aromatic hydrocarbons are used and the extraction is carried out at a pH of from 2.0 to 6.0.

The novel process has the advantage that the extraction proceeds smoothly and the oligomers present no problems.

The aqueous solutions to be extracted as a rule contain from 2 to 20% by weight of caprolactam and from 15 to 25% by weight, based on the organic compounds present in the aqueous solution, of caprolactam oligomers. Particularly preferred solutions contain from 3 to 10% by weight of caprolactam and the corresponding amounts of oligomers. Such solutions are obtained, for example, by extracting polycaprolactam with water, as described, for example, in German Pat. No. 2,242,641. In addition, caprolactam-containing aqueous solutions of other origin may also be present when carrying out the extraction, for example aqueous solutions obtained from the extraction of crude lactam.

The extraction according to the invention is carried out with liquid aromatic hydrocarbons, eg. benzene, xylene or toluene, benzene and toluene being preferred. Advantageously, from 2 to 12, in particular from 2.5 to 10, parts by weight of liquid aromatic hydrocarbons are employed per part by weight of aqueous solution. The extraction is preferably carried out at from 30° to 70° C. and under atmospheric pressure or slightly superatmospheric pressure, for example at up to 1.5 bar.

According to the invention, the extraction is carried out at a pH of from 2.0 to 6.0, especially from 2.5 to 5.0. If only wash waters containing caprolactam and its oligomers are used, these are advantageously acidified to the above pH, prior to the extraction, with a non-oxidizing mineral acid, such as sulfuric acid or phosphoric acid, especially the former. If, in addition, caprolactam-containing aqueous solutions resulting from the extraction of crude lactam, for example according to German Pat. No. 1,194,863, are present, acidification is unnecessary, since the latter aqueous solutions already have, per se, the desired pH.

An advantageous procedure is to introduce the aqueous solution, containing caprolactam and its oligomers, into the upper one-fifth of the extraction zone and the liquid aromatic hydrocarbon into the lower one-fifth, and to take off a solution of caprolactam in the liquid aromatic hydrocarbons at the upper end of the column and an aqueous phase, containing caprolactam oligomers, at the lower end. The extraction is advantageously carried out in conventional extraction columns, for example perforated tray columns, packed columns, pulsed packed columns or stirring disk columns. Suitable columns have, for example, from 10 to 50 theoretical plates.

The resulting solution of caprolactam in liquid aromatic hydrocarbons, which contains, for example, from 0.5 to 8% by weight of caprolactam, is advantageously used as an extractant in the extraction of crude lactam described in German Pat. No. 2,656,182. The caprolactam oligomers can be isolated from the aqueous phase and, for example, be converted to monomeric caprolactam by thermal cleavage.

The Example which follows illustrates the invention.

EXAMPLE

The preparation of caprolactam by a Beckmann rearrangement gives a crude lactam which is purified by extraction with benzene. The resulting benzene/lactam phase is worked up to give caprolactam. A brown solution, containing ammonium sulfate, impurities and a small amount of caprolactam, is obtained as the aqueous phase.

10 t per hour of this brown aqueous phase, containing 1.0% by weight of lactam and having a pH of 4.2, are fed to the uppermost of 25 trays of a perforated tray column of 2,500 mm diameter. 50,549 kg per hour of benzene are fed to the lowest tray. The temperature in the extraction column is 60°–65° C. Additionally, 10 m$^3$ per hour of extraction water from nylon manufacture, containing 4% of caprolactam and 0.8% of oligomers, and having a pH of 5.1, are also fed, at 60°–65° C., to the uppermost tray.

At the upper end of the extraction column, 51,111 kg per hour of a benzene/lactam solution containing 0.9% of lactam, 0.2% of H$_2$O and 98.9% of benzene are obtained. This solution is employed for the extractive purification of the crude lactam and the benzene is then distilled off and re-used for extracting the aqueous phase described.

At the lower end of the column, 20 t per hour of a brown aqueous phase are obtained, containing ammonium sulfate, impurities, 0.2% of caprolactam and 0.4% of oligomers. The pH is 4.6. This solution is steam-stripped to remove benzene, the latter being recycled. The solution which has been freed from benzene can be subjected to biological treatment or be concentrated and then burnt. Even after 4 months' operation, no problems due to blockages of the perforated trays arise.

We claim:

1. In a process for continuously extracting caprolactam from an aqueous solution, containing caprolactam and its oligomers, with organic solvents, by introducing the aqueous solution into the upper part of an extraction zone and organic solvents into the lower part, and taking off a solution of caprolactam in organic solvents at the upper end and an aqueous phase containing caprolactam oligomers at the lower end, the improvement that liquid aromatic hydrocarbons are used and the extraction is carried out at a pH of from 2.0 to 6.0.

2. The process set forth in claim 1, wherein benzene or toluene is used as the solvent.

3. The process set forth in claim 1, wherein the pH is kept at from 2.5 to 5.0.

4. The process set forth in claim 1, wherein from 2 to 12 parts by weight of benzene or toluene are used per part by weight of aqueous solution.

* * * * *